(12) United States Patent
Yokota et al.

(10) Patent No.: US 6,774,627 B2
(45) Date of Patent: Aug. 10, 2004

(54) LEAK MAGNETISM DETECTION SENSOR FOR MAGNETIC FLAW DETECTION SYSTEM

(75) Inventors: Hiroyuki Yokota, Chiba (JP); Yasuo Tomura, Chiba (JP); Hideaki Unzaki, Chiba (JP); Shigetoshi Tsuruoka, Tokuyama (JP)

(73) Assignees: Kawasaki Steel Corporation, Kobe (JP); System Hitec, Ltd., Tokuyama (JP)

( * ) Notice: Subject to any disclaimer, the term of this patent is extended or adjusted under 35 U.S.C. 154(b) by 0 days.

(21) Appl. No.: 10/168,095

(22) PCT Filed: Oct. 18, 2001

(86) PCT No.: PCT/JP01/09159
§ 371 (c)(1),
(2), (4) Date: Aug. 26, 2002

(87) PCT Pub. No.: WO02/33398
PCT Pub. Date: Apr. 25, 2002

(65) Prior Publication Data
US 2003/0038629 A1 Feb. 27, 2003

(30) Foreign Application Priority Data
Oct. 18, 2000 (JP) .................... 2000-317711
Sep. 28, 2001 (JP) .................... 2001-299768

(51) Int. Cl.$^7$ .................... G01N 27/83; G01R 33/12
(52) U.S. Cl. .................... 324/242; 324/235
(58) Field of Search .................... 324/228, 242

(56) References Cited

U.S. PATENT DOCUMENTS

| | | | |
|---|---|---|---|
| 5,089,776 A | * | 2/1992 | Furukawa et al. .......... 324/227 |
| 5,357,198 A | | 10/1994 | Ando et al. |
| 5,502,382 A | | 3/1996 | Ando et al. |
| 5,706,572 A | * | 1/1998 | Garshelis .................... 29/602.1 |
| 5,793,200 A | * | 8/1998 | Berrill ..................... 324/207.2 |
| 6,037,767 A | * | 3/2000 | Crescenzo et al. .......... 324/220 |
| 6,057,684 A | * | 5/2000 | Murakami et al. .......... 324/240 |
| 6,266,983 B1 | * | 7/2001 | Takada et al. ............... 72/11.1 |

FOREIGN PATENT DOCUMENTS

| | | | | |
|---|---|---|---|---|
| CA | 2079774 | | 8/1992 | |
| EP | 0 523 249 A1 | | 1/1993 | |
| JP | A 58-153157 | | 9/1983 | |
| JP | 03039466 A | * | 2/1991 | .......... C23C/14/30 |
| JP | U 7-38956 | | 7/1995 | |
| JP | A 8-327603 | | 12/1996 | |
| JP | 10293121 A | * | 11/1998 | .......... G01N/27/83 |
| JP | A 2002-195984 | | 7/2002 | |
| JP | 2003107056 A | * | 4/2003 | .......... G01N/27/83 |
| WO | WO 92/14145 | | 8/1992 | |

\* cited by examiner

*Primary Examiner*—Jay Patidar
*Assistant Examiner*—Darrell Kinder
(74) *Attorney, Agent, or Firm*—Oliff & Berridge, PLC

(57) ABSTRACT

A soft-magnetic material is installed on the opposite side of the magnetism sensing face of magnetism sensing devices. This soft-magnetic material is larger than the magnetism sensing face. Then the detection coverage per sensor is enlarged, and the number of sensors and signal processing circuits are reduced across the width of the strip.

5 Claims, 6 Drawing Sheets

LEAK MAGNETISM DETECTION SENSOR FOR MAGNETIC FLAW DETECTION SYSTEM

TECHNICAL FIELD

This invention relates to leak magnetism detection sensors for use in magnetic flaw detection systems, and particularly, it relates to a leak magnetism detection sensor for the online magnetic flaw detection system that is suitable for use in leakage flux sensing for detecting surface flaws and inclusions of a steel strip by sensing the leakage flux arising from the internal and surface of the ferromagnetic object under test.

BACKGROUND ART

The flaw detection technique using leakage flux is a method for detecting defect by generating a magnetic field along the traveling direction of the target object and then sensing the leakage flux arising from internal and surface defects of the object. As sensors for detecting leakage flux, there are semiconductor-type magnetic sensors such as magnetic diodes, magneto-resistance devices and Hall devices, and the coil-type ones such as planar coils and induction coil sensors that hold coils wound on ferrite.

Among them, the magnetic diode has the advantages of being high in sensitivity and small in size. On the other hand, it has the disadvantages of having poor temperature characteristics, large inherit noise and low mechanical strength.

The coil-type sensors have simple structures and good temperature characteristics, while they have a disadvantage of being low in sensitivity.

Meanwhile, the Hall device, which was a low-sensitivity semiconductor magnetic sensor, has come to have improved sensitivity and temperature characteristics, thus being widely adopted as a leak magnetism detection sensor for use in the flaw detection using leakage flux.

Tin plates, which are employed in food cans, are strongly worked during the production of two-piece cans (DI cans). Thus non-metallic inclusions inside the material (hereafter, simply referred to as inclusions) cause cracks during working. The target for sensing is a volume of $0.5 \times 10^{-3}$ mm$^3$, assuming an elliptic region of, approximately, 1.0 mm long, 0.1 mm wide and 0.01 mm thick. Thus there are such problems that as many as around 1000 semiconductor magnetic sensors are needed to perform an online flaw detection over the full width of the target and that a huge number of signal processing circuits for as many as 1000 channels must be prepared.

An invention similar to this invention is disclosed in Japanese Utility Model Laid-Open Publication No. Hei. 7-38956. In that disclosure, a ferromagnetic material is directly attached to the opposite side of the magnetism sensing face of a coil sensor where a coil is formed on the magnetism sensing surface, in order to enhance the sensor sensitivity by gathering leakage flux in the ferromagnetic material and rendering most of the gathered magnetic flux intersect the magnetism sensing face of the coil sensor. However, it does not refer to the expansion of detection coverage of the sensor.

Japanese Patent Laid-Open Publication No. Hei. 4-296648 has also disclosed a ferromagnetic jig installed near a magnetic sensor. This jig is a magnetic shield prepared for reducing magnetic flux around the magnetic sensor so that the high density of magnetic flux in the surrounding space bypasses the magnetic sensor and thereby the magnetic sensor may not saturate. This jig is expected to improve sensor sensitivity to some extent but does not aim to expand the detection coverage.

SUMMARY OF THE INVENTION

This invention has been made to solve those conventional problems and aims to reduce the number of sensors and signal processing circuits by expanding the detection coverage of each leak magnetism detection sensor.

In order to solve the problems mentioned above, according to this invention, a leak magnetism detection sensor, which is used in a magnetic flaw detection system that generates a magnetic field along a traveling direction of a target strip and detects online leakage flux arising from internal and surface defects of the target strip with a flaw detection head equipped with a number of magnetism sensing devices arrayed across the width of the target strip to provide signals indicating the existence of defects, has a soft-magnetic material that is installed on an opposite side of the magnetism sensing face of a magnetism sensing devices and is larger than the magnetism sensing face.

Further, each of the magnetism sensing devices is located apart from the soft-magnetic material and has another soft-magnetic material kept contact with the opposite side of the magnetism sensing face of the magnetism sensing device.

Still further, the magnetism sensing device has another soft-magnetic material kept contact with its magnetism sensing face.

Yet further, the magnetism sensing device is a Hall device.

In addition, the present invention provides a method of detecting online flaws in strips, using a leak magnetism detection sensor comprising a number of magnetism sensing devices arrayed across a width of a target strip for detecting leakage flux arising from internal and surface defects thereof and a soft-magnetic material that is installed on an opposite side of a magnetism sensing face of the magnetism sensing devices and is larger than the magnetism sensing face.

FIG. 1 shows the leak magnetism detection sensor of the present invention (for example, a semiconductor sensor). In this leak magnetism detection sensor, a soft-magnetic material 14 that has a permeability much higher than that of air and is larger than a magnetism sensing face 12A of a magnetism sensing device (for example, a Hall device) of a semiconductor magnetic sensor 12 is installed on the opposite side of this magnetism sensing face 12A, namely, on the-other side of the sensor facing the target strip, apart from this magnetism sensing face 12A at a predetermined distance, namely apart from the magnetism sensing device. Then the soft-magnetic material 14 attracts leakage flux F arising from an inclusion 10A in a steel strip 10. As a result, the coverage of each sensor becomes larger and its sensitivity is enhanced because more of the magnetic flux F is concentrated to intersect the magnetism sensing face 12A in the direction perpendicular to both magnetism sensing face 12A and strip 10.

As shown in FIG. 2, the semiconductor magnetic sensor 12 shown in FIG. 1 may have a magnetism sensing device 12C such as a Hall device on the surface of a soft-magnetic material 12B such as ferrite. Namely, the soft-magnetic material 12B is kept contact with the opposite side of the magnetism sensing face of the magnetism sensing device 12C. Seen from the target strip 10, the semiconductor magnetic sensor 12 holding the magnetism sensing device 12C on the side facing the strip 10 and the soft-magnetic material 14 are installed in this order. Then since further more of the leakage flux F is concentrated to intersect the magnetism sensing face 12A at right angles as shown in FIG. 3, the detection coverage of each sensor is expanded and its sensitivity is enhanced in this further preferable example. Reference numeral 16 in FIG. 2 denotes a supporting plate for sensor mounting.

Higher sensitivity is provided by the following mechanism. When the magnetism sensing device 12C such as a Hall device is mounted on the soft-magnetic material 12B such as ferrite as shown in FIG. 2, more of the leakage flux F gathered by the aforementioned soft-magnetic material 14 is further gathered in the magnetism sensing face 12A by the soft-magnetic material 12B used in the semiconductor magnetic sensor 12. As a result, more of the leak flux F comes to intersect the magnetism sensing face 12A in the direction normal thereto.

As shown in FIG. 4, the semiconductor sensor may have the magnetism sensing device 12C such as a Hall device on the surface of the soft-magnetic material 12B such as ferrite and may sandwich this magnetism sensing device 12C such as a Hall device between soft-magnetic materials 12B and 12D such as ferrite by installing a soft-magnetic material 12D like ferrite adhered to the magnetism sensing face 12A of the magnetism sensing device like a Hall device. As a result, the magnetism sensing face is protected and the sensitivity is further raised since the leakage flux F intersects the magnetism sensing face 12A in the direction normal thereto.

It is preferable to employ a Hall device as the magnetism sensing device 12C. Since the Hall device has a low noise level, it can easily detect such small inclusions that are referred to in this invention. In addition, since a small Hall device can be made very thin, it enables to downsize the leak magnetism detection sensor of the configuration in accordance with this invention particularly in the direction perpendicular to the surface of the strip. As a result, the Hall device makes it easier to shorten the distance between the magnetism sensing face and the target strip during measurement and to raise sensing accuracy, compared with other magnetism sensing devices.

In contrast, the leakage flux presents a distribution shown in FIG. 5 in the conventional configuration having a sensor element alone. Leakage flux F crosses the magnetism sensing face 12A of the sensor 12 at shallow angles. Then since the portion of magnetic flux normal to the magnetism sensing face 12A is small, the detection coverage per sensor is small.

DETAILED DESCRIPTION OF EXEMPLARY EMBODIMENTS

Now an embodiment of the present invention is described in detail with reference to the accompanying drawings.

Figure 1:
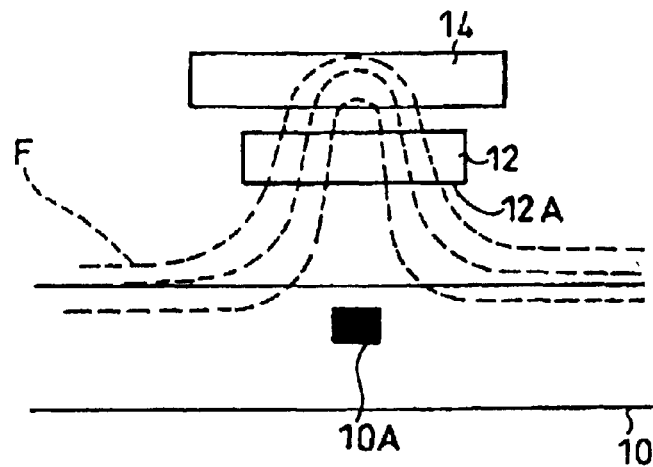
FIG. 1 is a sectional view illustrating the principle of the present invention.
Figure 2:
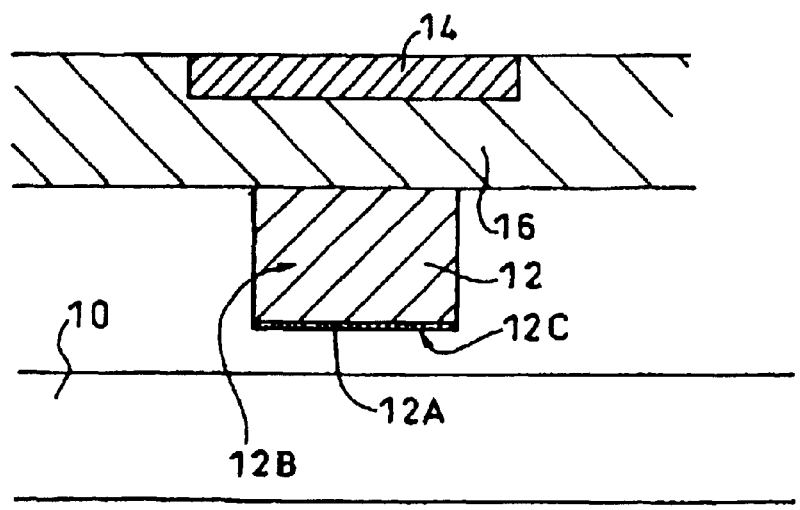
FIG. 2 is a sectional view illustrating the structure of the semiconductor magnetic sensor in accordance with an improved example of the invention.
Figure 3:
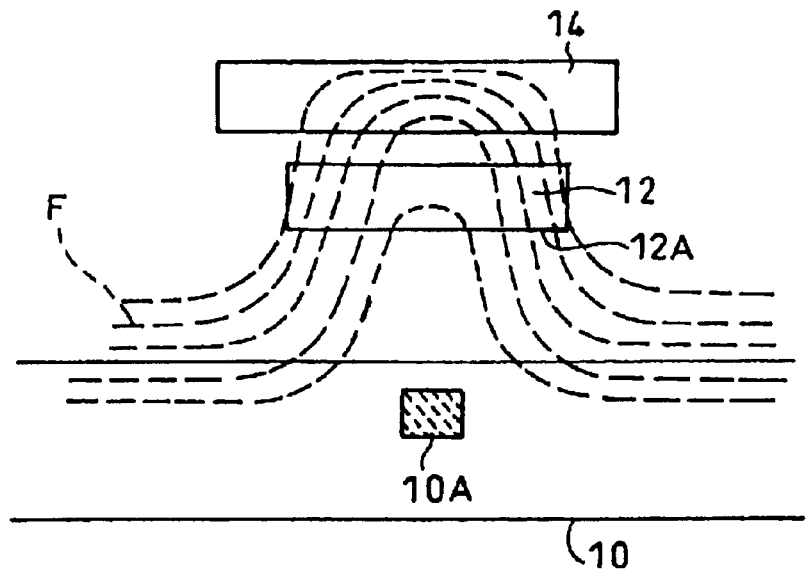
FIG. 3 is a sectional view illustrating the principle of the improved example.
Figure 4:
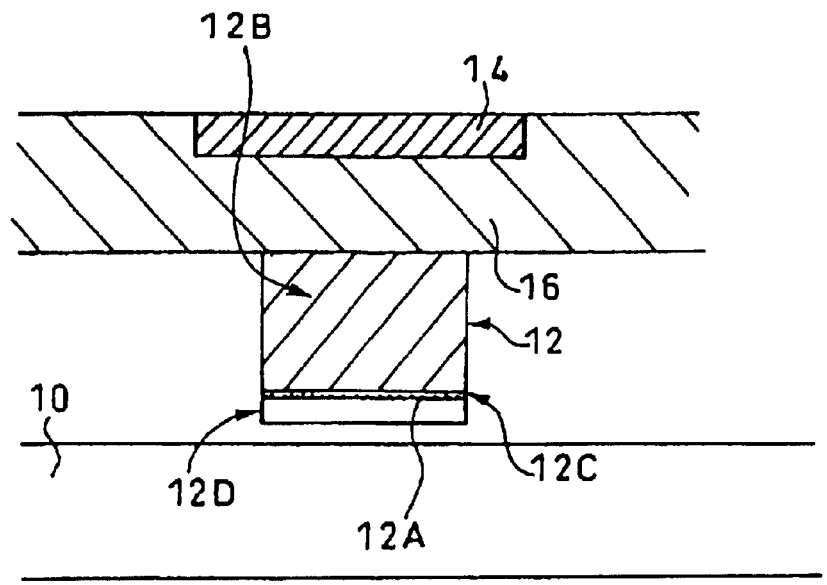
FIG. 4 is a sectional view illustrating the structure of the semiconductor magnetic sensor in accordance with another improved example of the invention.
Figure 5:
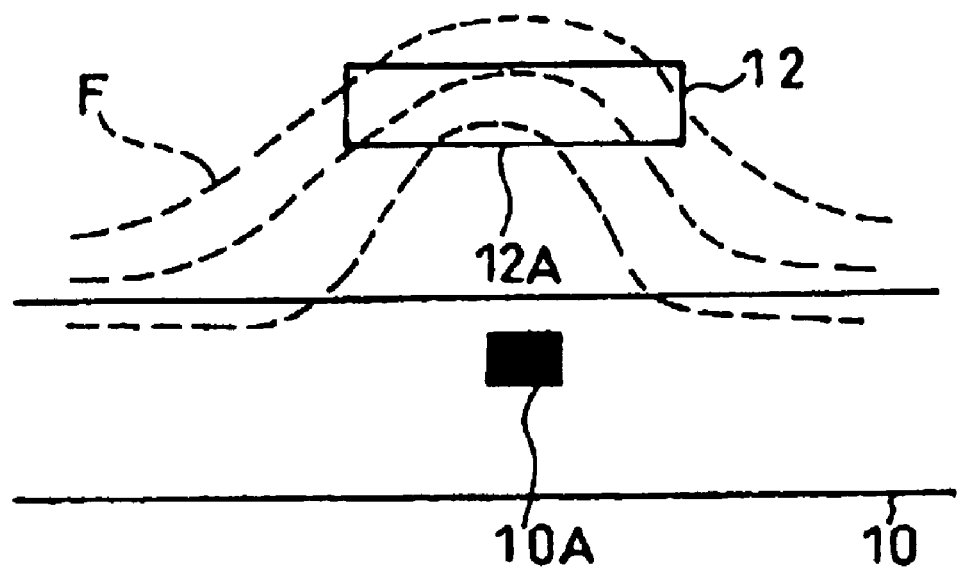
FIG. 5 is a sectional view illustrating the conventional principle.
Figure 6:
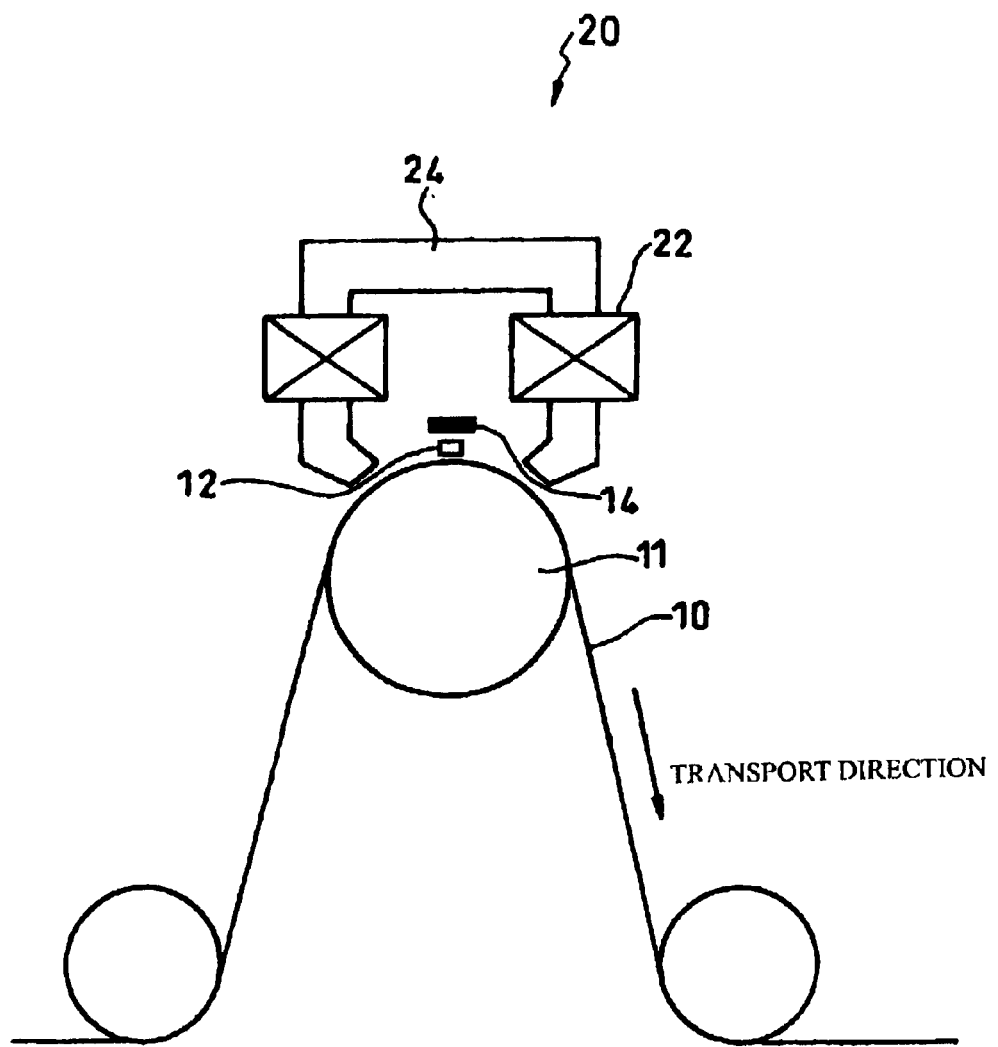
FIG. 6 is a sectional view illustrating the whole configuration of an embodiment of the present invention.
Figure 7:
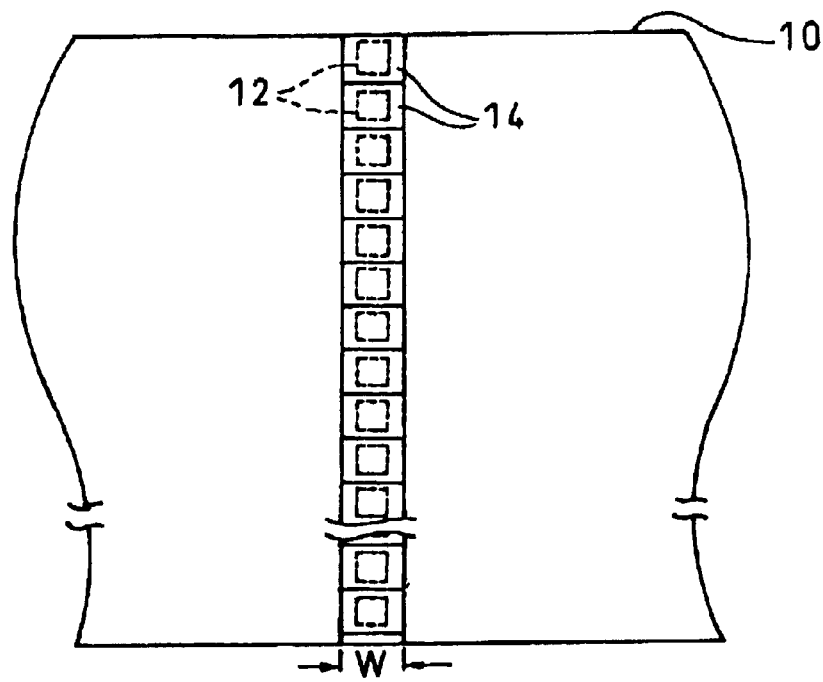
FIG. 7 is its plan view.
Figure 8:
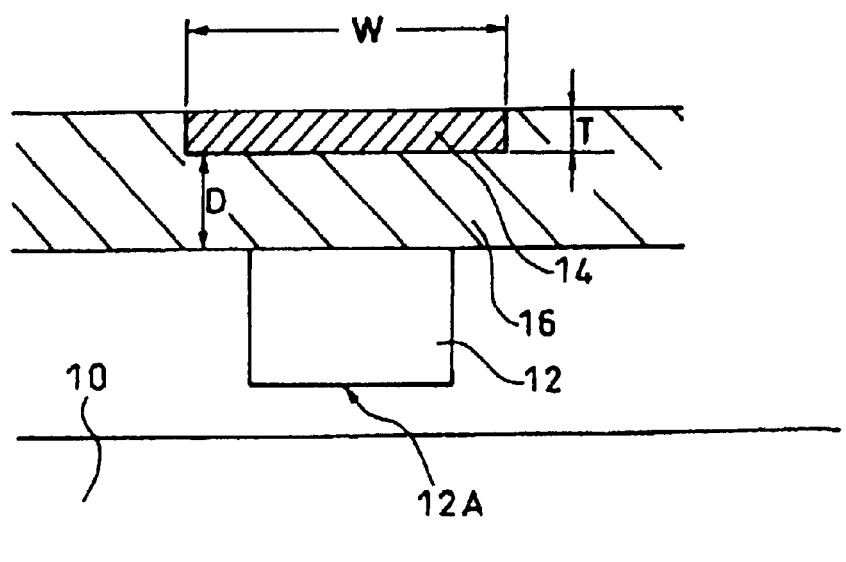
FIG. 8 is a sectional view illustrating the structure of the semiconductor magnetic sensor.

FIG. 6 is a schematic view illustrating the whole configuration of the embodiment of the present invention; FIG. 7 is its plan view; and FIG. 8 is a sectional view illustrating the geometries of the semiconductor magnetic sensor (Hall device in this example) and the soft-magnetic material that constitute the leak magnetism detection sensor in accordance with the present invention.

Referring now to FIG. 6, the semiconductor magnetic sensor 12, soft-magnetic material 14 and magnetizing yoke 24 where magnetizing coils 22 are wound for magnetizing the strip 10 according to the present invention are integrated into a magnetic sensor head 20 and installed in the vicinity of a non-magnetic roll 11 that conveys the strip 10 in the direction shown by the arrow.

When a DC current runs in the magnetizing coil 22, the magnetizing yoke 24 magnetizes the strip 10. Then if the strip 10 has inclusions and/or surface flaws, leakage flux appears. This leakage flux is collected by the soft-magnetic material 14 that is larger than the magnetism sensing face 12A of the semiconductor magnetic sensor 12 and concentrated to intersect the magnetism sensing face 12A of the semiconductor magnetic sensor 12. Then the detection coverage of each sensor can be enlarged.

FIG. 7 is a schematic diagram illustrating the geometries of the semiconductor magnetic sensor 12 and the soft-magnetic material 14 mounted on the opposite side of the magnetism sensing face 12A. The leak magnetism detection sensor according to the present invention includes the semiconductor magnetic sensor 12 and the soft-magnetic material 14 that is buried in the supporting plate 16 for mounting and has a width, W, which is larger than that of the magnetism sensing face 12A.

In case of the present embodiment using a magnetic sensor of the integrated structure, a horizontal magnetic field is created between the poles of the yoke 24 even when the strip under test is standing still. Because this floating magnetic field exerts a negative effect on magnetic materials, this embodiment employs a soft-magnetic material that has strong magnetized characteristics and allows a high flux density.

The preferable geometry and the mounting position of the soft-magnetic material 14 change with the size of defects in the target object. For example, the soft-magnetic material may be, approximately, 1–10 mm in width W and 0.05–3 mm in thickness T; and it may be installed at a distance, D, of 0.1–3 mm from the opposite side of the magnetism sensing face 12A of the semiconductor magnetic sensor 12. As shown in FIG. 7, the soft-magnetic material may be as wide as the full width of the employed sensor.

As mentioned before, it is necessary to make the soft-magnetic material 14 larger than the magnetism sensing face 12A, preferably as much as 5–30 times each of lengths in longer and shorter axis directions of the magnetism sensing face. At the same time, the soft-magnetic material 14 may preferably be located in the center of the width of the projection of the magnetism sensing face 12A onto the soft-magnetic material 14.

In this embodiment, it is easy to make the sensor structure simple because the soft-magnetic material 14 is buried in the supporting plate 16 prepared for sensor mounting. The location of the soft-magnetic material, however, is not limited to the above example. The soft-magnetic material 14 may be other than ferrite, for example, inexpensive materials such as cold rolled steel sheet (annealed steel sheet).

Besides, the whole structure is simple in this embodiment because the semiconductor magnetic sensor 12 and soft-magnetic material 14 are integrated into the magnetic sensor head 20 together with the magnetizing coils 22 and magnetizing yoke 24. It is, however, possible to separate the magnetizing coils 22 and magnetizing yoke 24 from the semiconductor magnetic sensor 12 and soft-magnetic material 14.

Then the results of an experiment that was conducted to make sure the effect of the present invention are described below. The performance of the invention was confirmed in a test where the integrated magnetic sensor head 20 of this embodiment was installed on an experimental roll that was able to repeat measurement of the same position.

In the test, a Hall device was employed as the magnetism sensing device and the semiconductor magnetic sensor employed this Hall device on the surface of ferrite. The employed soft-magnetic material 14 was a cold rolled steel plate that was larger than the magnetism sensing face of the magnetism sensing device, namely, 10 times each of the lengths in the longer and shorter axis directions of the magnetism sensing face.

Figure 9:
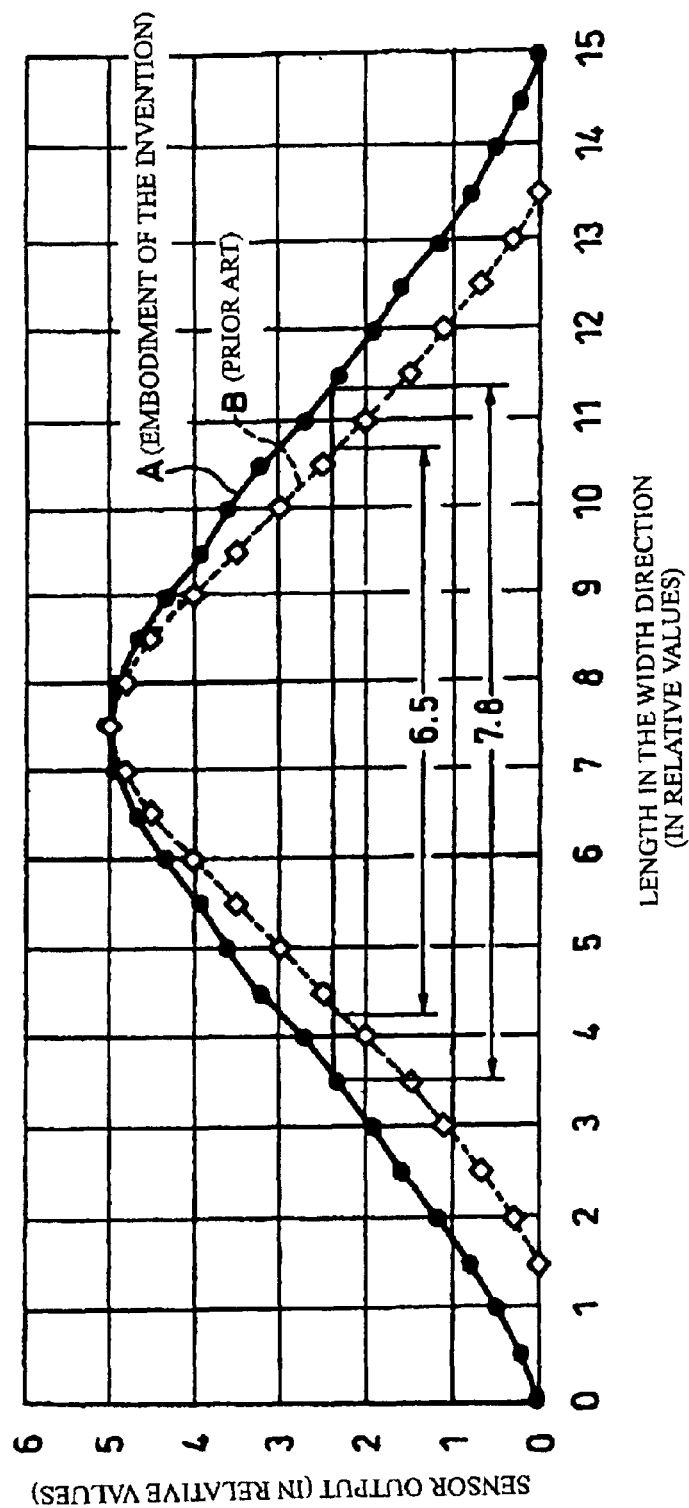
FIG. 9 is a graph illustrating the results of a test that was conducted to confirm the effect of the invention.

The target object for measurement was a 0.23 mm-thick tin plate made from continuous casting material, having an inclusion that was 1.0 mm long, 0.1 mm wide and approximately 0.01 mm thick. The rotation speed of the roll was set at 200 mpm and the liftoff between the magnetic sensor and the target object was set at 1.0 mm. The magnetic sensor head 20 was moved rightward at 0.2 mm pitches from the position corresponding to the left end of the lateral axis of FIG. 9 to measure the inclusion that repeatedly passed the same position. The measurements were carried out with the soft-magnetic material 14 (solid line A) and without such a soft-magnetic material like the case of a conventional sensor (broken line B). Then as shown in FIG. 9, the width at half the peak value (half width) changed according to the presence/absence of the soft-magnetic material 14. The half width (7.8) for the case having the soft-magnetic material 14 was about 20% larger than that (6.5) for the case having no soft-magnetic material. Thus, it would be possible to reduce the number of sensors and signal processing circuits about 20%.

Furthermore, the fluctuations in sensor output caused by changes in the magnetizing current or the current running in the magnetizing coil were studied according to the presence/absence of the soft-magnetic material 14.

In general, the sensor output of magnetism sensing devices such as Hall devices grows proportionally as the magnetizing current rises, and the sensor output tends to saturate after the magnetizing current has reached a certain level.

As is the case with the present embodiment, when the semiconductor sensor employs a Hall device mounted on ferrite, the sensor output saturates at a lower magnetizing current, compared with the case using a Hall device alone. Then, the sensor output tends to become smaller as the magnetizing current is increased.

Meanwhile, when such a semiconductor sensor employs the soft-magnetic material 14, the sensor output does not saturate until the magnetizing current has reached a higher value and thus it is confirmed that the sensor output at saturation becomes larger, compared with the case of having no soft-magnetic material 14. If the sensor output does not saturate until the magnetizing current has reached a large value, it is possible to run a large magnetizing current during measurement. In other words, it is confirmed that the sensor is able to measure target objects that are rather thick.

Besides, the sensor output itself becomes large and thereby it is confirmed that the measurement accuracy can be improved.

At around the magnetizing current causing the saturation of sensor output, the changes in sensor output with respect to magnetizing current become smaller in the presence of the soft-magnetic material 14 than those in its absence, and thus it is also confirmed that reliable measurements can be conducted.

In the above descriptions, the present invention was used in the online flaw detection for steel sheets. This invention, however, can be adopted in other applications. The leak magnetism detection sensor is preferably a semiconductor magnetic sensor using the Hall device. However, the leak magnetism detection sensor may be other than this type.

Since this invention expands the detection coverage per leak magnetism detection sensor, the number of sensors and signal processing circuits can be reduced. Moreover, since the sensor sensitivity is enhanced, it is possible to detect micro inclusions even if the liftoff is set at a large value, for example, 1 mm.

What is claimed is:

1. A leak magnetism detection sensor for a magnetic flaw detection system that generates a magnetic field along a traveling direction of a target strip and detects online leakage flux arising from internal and surface defects of the strip with a flaw detection head equipped with a number of magnetism sensing devices arrayed across a width of the strip to provide signals indicating existence of defects, characterized in that, a soft-magnetic material is installed on an opposite side of a magnetism sensing face of said magnetism sensing devices and is larger than said magnetism sensing face.

2. The leak magnetism detection sensor for a magnetic flaw detection system according to claim 1, characterized in that each of said magnetism sensing devices is located apart from said soft-magnetic material and another soft-magnetic material is installed to be kept in contact with the opposite side of the magnetism sensing face of said magnetism sensing device.

3. The leak magnetism detection sensor for a magnetic flaw detection system according to claim 2, characterized in that still another soft-magnetic material is installed to be kept contact with the magnetism sensing face of said magnetism sensing device.

4. The leak magnetism detection sensor for a magnetic flaw detection system according to claim 1, characterized in that said magnetism sensing device is a Hall device.

5. A method of detecting flaws online in strips, characterized by using a leak magnetism detection sensor comprising a number of magnetism sensing devices arrayed across a width of a target strip for detecting leakage flux arising from internal and surface defects thereof, and a soft-magnetic material that is installed on an opposite side of a magnetism sensing face of said magnetism sensing devices and is larger than said magnetism sensing face.

* * * * *